(12) United States Patent
Abbott

(10) Patent No.: US 9,840,446 B2
(45) Date of Patent: Dec. 12, 2017

(54) PROCESS FOR PRODUCTION OF METHANE-CONTAINING GAS MIXTURE

(71) Applicant: JOHNSON MATTHEY PUBLIC LIMITED COMPANY, London (GB)

(72) Inventor: Peter Edward James Abbott, Cleveland (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/303,928

(22) PCT Filed: Mar. 20, 2015

(86) PCT No.: PCT/GB2015/050840
§ 371 (c)(1),
(2) Date: Oct. 13, 2016

(87) PCT Pub. No.: WO2015/159044
PCT Pub. Date: Oct. 22, 2015

(65) Prior Publication Data
US 2017/0022121 A1    Jan. 26, 2017

(30) Foreign Application Priority Data
Apr. 16, 2014 (GB) .................................. 1406890.2

(51) Int. Cl.
*C07C 1/04* (2006.01)
*C07C 7/148* (2006.01)
(Continued)

(52) U.S. Cl.
CPC .............. *C07C 1/0435* (2013.01); *C07C 1/04* (2013.01); *C07C 1/12* (2013.01); *C07C 7/14816* (2013.01);
(Continued)

(58) Field of Classification Search
CPC    C07C 1/04; C07C 1/12; C07C 1/0435; C07C 2523/755; C07C 2523/46; C10K 3/02; C10G 2/32; C10L 3/08; C10L 3/101
See application file for complete search history.

(56) References Cited

U.S. PATENT DOCUMENTS 4,205,961 A    6/1980  Moller et al.
4,242,105 A    12/1980 Frost
(Continued)

FOREIGN PATENT DOCUMENTS

| EP | 2 684 856 A1 | 1/2014 |
|---|---|---|
| WO | 2011/034891 A1 | 3/2011 |
| WO | 2012/001401 A1 | 1/2012 |

OTHER PUBLICATIONS

Janicke et al., "The Controlled Oxidation of Hydrogen from an Explosive Mixture of Gases Using a Microstructured Reactor/Heat Exchanger and Pt/Al2O3 Catalyst," Journal of Catalysis, Academic Press, Apr. 25, 2000, pp. 282-293, vol. 191, No. 2, Duluth, MN, US.

(Continued)

*Primary Examiner* — Jafar Parsa
(74) *Attorney, Agent, or Firm* — Baker & Hostetler LLP

(57) ABSTRACT

A process for producing a methane-containing gas mixture includes the steps of:
(i) passing a first feed gas mixture including hydrogen and carbon dioxide through a bed of methanation catalyst to react a portion of the hydrogen with at least a portion of the carbon dioxide and form a methane-containing gas mixture containing residual hydrogen,
(ii) adding an oxygen-containing gas to the methane-containing gas mixture containing residual hydrogen to form a second feed gas mixture, and
(Continued)

(iii) passing the second feed gas mixture through a bed of an oxidation catalyst to react the residual hydrogen and oxygen to form a hydrogen depleted methane-containing gas mixture.

13 Claims, 1 Drawing Sheet

(51) Int. Cl.
| | | |
|---|---|---|
| *C07C 1/12* | (2006.01) | |
| *C10G 2/00* | (2006.01) | |
| *C10L 3/08* | (2006.01) | |
| *C10L 3/10* | (2006.01) | |
| *C10K 3/02* | (2006.01) | |

(52) U.S. Cl.
CPC ................ *C10G 2/332* (2013.01); *C10K 3/02* (2013.01); *C10L 3/08* (2013.01); *C10L 3/101* (2013.01); *C07C 2523/46* (2013.01); *C07C 2523/755* (2013.01); *C10L 2290/141* (2013.01)

(56) References Cited

U.S. PATENT DOCUMENTS

2010/0287836 A1    11/2010  Robinson et al.
2013/0055637 A1*  3/2013  Ariyapadi .................. C10J 3/00
                                                              48/119

OTHER PUBLICATIONS

Van Der Meijden et al., "The Production of Synthetic Natural Gas (SNG): A Comparison of Three Wood Gasification Systems for Energy Balance and Overall Efficiency," Biomass and Bioenergy, Pergamon, Mar. 1, 2010, pp. 302-311, vol. 34, No. 3, Amsterdam, NL.

International Search Report issued in Application No. PCT/GB2015/050840, dated Jun. 5, 2015.

* cited by examiner

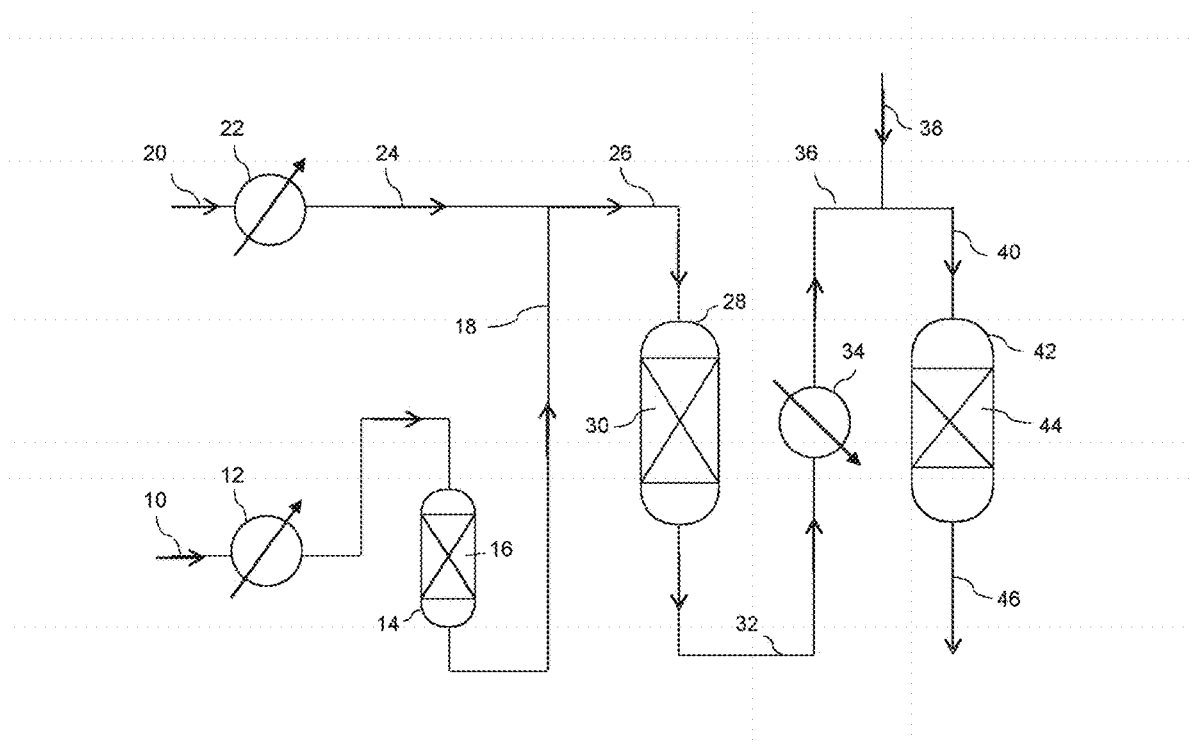

PROCESS FOR PRODUCTION OF METHANE-CONTAINING GAS MIXTURE

PROCESS

This invention relates to a process for preparing a methane-containing gas mixture.

Processes for making methane containing gas mixtures by methanation of a synthesis gas comprising carbon dioxide, carbon monoxide and hydrogen are described for example in WO2012001401 (A1).

However there is a need for processes to provide methane-containing gas streams with lower residual levels of hydrogen than may be achieved using methanation alone.

Accordingly, the invention provides a process for producing a methane-containing gas mixture comprising the steps of:
  (i) passing a first feed gas mixture comprising hydrogen and carbon dioxide through a bed of methanation catalyst to react a portion of the hydrogen with at least a portion of the carbon dioxide and form a methane-containing gas mixture containing residual hydrogen,
  (ii) adding an oxygen-containing gas to the methane-containing gas mixture containing residual hydrogen to form a second feed gas mixture, and
  (iii) passing the second feed gas mixture through a bed of an oxidation catalyst to react the residual hydrogen and oxygen to form a hydrogen depleted methane-containing gas mixture.

The first feed gas mixture may be a synthesis gas comprising hydrogen, carbon dioxide and carbon monoxide. The synthesis gas may be formed from the gasification of carbonaceous feedstocks, such as coal or biomass using conventional techniques. Alternatively, the synthesis gas may be prepared by pre-reforming, steam reforming, or by autothermal reforming or catalytic partial oxidation of hydrocarbons such as natural gas or naphtha. The synthesis gas may also contain methane and may already have been subjected to one or more stages of methanation upstream.

Alternatively, the first feed gas mixture may be prepared by mixing a hydrogen-containing gas mixture with a carbon dioxide-containing gas mixture. The hydrogen containing gas mixture may be a synthesis gas or may be another gas stream containing hydrogen such as a methane-containing gas mixture. The carbon dioxide-containing gas mixture may be any suitable gas comprising or consisting essentially of carbon dioxide.

Alternatively, the first feed gas mixture may be provided by a coupling reactor designed to oxidatively couple methane to produce ethylene. This reaction may only give partial conversion in one pass and hence it may be necessary to recycle unreacted gases which contain carbon dioxide, hydrogen and unreacted methane recovered downstream of the reactor, back to the inlet of the coupling reactor to improve the overall reaction yield. In such a case it is not desirable to have hydrogen in the feed to the reactor as it will react with the oxygen in preference to the methane.

In a process, where the objective is to minimise the hydrogen concentration in the product methane-containing gas mixture, it is desirable for the carbon dioxide and any carbon monoxide to be present in an amount more than that theoretically required to methanate all of the hydrogen. The methanation reactions for carbon monoxide and carbon dioxide may be written as follows:

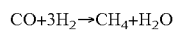

$CO + 3H_2 \rightarrow CH_4 + H_2O$

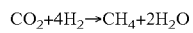

$CO_2 + 4H_2 \rightarrow CH_4 + 2H_2O$

Consequently, for a first feed gas containing carbon monoxide, carbon dioxide and hydrogen for x mols/hr of CO and y mols/hr CO2, and z mols/hr H2; preferably z<(3x+4y). Furthermore, it is desirable that the hydrogen concentration in the first feed gas mixture is ≤20% vol and preferably ≤15% vol.

It may be desirable, in order to prevent catalyst poisoning, to subject the first feed gas mixture or the hydrogen-containing gas mixture and/or the carbon dioxide-containing gas mixture to a desulphurisation step prior to the methanation step. For example the first feed gas mixture or the hydrogen-containing gas mixture and/or the carbon dioxide-containing gas mixture may be passed over a bed of a particulate zinc oxide desulphurisation material. Suitable inlet temperatures for desulphurisation are in the range 100-300° C. A particularly effective zinc oxide desulphurisation material is Puraspec™ 2020, available from Johnson Matthey PLC. If desired, the hydrogen-containing gas mixture or the first feed gas mixture may also be subjected to a step of hydrodesulphurisation by passing it over a hydrodesulphurisation (HDS) catalyst upstream of the zinc oxide desulphurisation material. In addition, should the first feed gas mixture contain unsaturated compounds (e.g. dienes or acetylenes) that might present coking problems, these could be removed by hydrogenation over a suitable hydrogenation catalyst, such as a copper catalyst, upstream of the methanation stage.

The methanation catalyst is desirably a nickel- or ruthenium-methanation catalyst, preferably a particulate nickel-containing methanation catalyst, more preferably a precipitated Ni catalyst with a Ni content ≥30% by weight, preferably ≥40% by weight. The methanation catalyst may be in the form of pellets or extrudates, but may also be a foam, monolith or coating on an inert support Pelleted methanation catalysts are preferred. Such catalysts are available commercially. A particularly suitable precipitated Ni catalyst with a Ni content 40% by weight is Katalco™ CRG-S2R, available from Johnson Matthey PLC.

Typically the methanation catalyst may be operated at an inlet temperature in the range 200-350° C., preferably 200-300° C., more preferably 230-280° C. The methanation step reacts hydrogen and carbon dioxide to form methane. Carbon monoxide present in the first feed gas mixture may also react with a portion of the hydrogen to form methane. A portion of the hydrogen in the feed remains unreacted, principally because there is an equilibrium limitation on the extent of conversion. The proportion of unreacted hydrogen in the methane containing gas mixture from the methanation step may be in the range 0.2 to 5 mole % of the second feed gas. The methanation reaction is exothermic and the reaction may be performed adiabatically in a fixed catalyst bed in a methanation vessel. The flow through the bed may be axial and/or radial flow. The methanation step may alternatively be operated with cooling of the catalyst bed, e.g. by passing at least a portion of the first feed gas mixture or the hydrogen-containing gas or the carbon dioxide containing gas through one or more tubes disposed within the catalyst bed.

In order to prevent unwanted side reactions it may be desirable to adjust the temperature of the methane-containing gas mixture containing residual hydrogen before mixing it with the oxygen containing gas. Where the methanation step is performed adiabatically it may be desirable to cool the methane containing gas mixture containing residual hydrogen. This may be performed by passing it through one or more shell and tube heat exchangers fed with water under pressure as the cooling medium, or by exchanging heat with the first feed gas in order to heat it up to the feed temperature for the methanation reactor.

The oxygen containing gas is preferably a relatively pure oxygen stream, containing >90% by volume $O_2$, but other oxygen-containing gases may be used, including air, if there is no significant disadvantage with the presence of extra nitrogen in the methane containing product gas.

In order to reduce the hydrogen content of the methanated gas, it is passed over an oxidation catalyst to selectively react the hydrogen with the oxygen in the oxygen containing gas to form water. Any carbon monoxide present in the second feed gas mixture may also be oxidised to form carbon dioxide. In the present invention the oxidation catalyst is selected to avoid oxidation of the methane formed in the methanation step. The oxidation reactions may be depicted as follows;

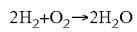

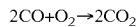

In order to ensure high conversion of the residual hydrogen, the oxygen containing gas may be added in stoichiometric excess, but too high an excess may cause unwanted side reactions. Consequently, the stoichiometric excess of oxygen to hydrogen and any carbon monoxide in the second feed gas mixture is preferably ≤50 mole % and more preferably ≤20 mole %.

If only petal conversion of the hydrogen is required, for example where the concentration of hydrogen needs to be reduced to ≤0.3% in the product gas, two options may be utilised;
  (i) the methane-containing gas mixture containing residual hydrogen can be split into a first portion and a second portion. The first portion may be combined with a stoichiometric excess of oxygen in the oxygen-containing gas to give almost complete hydrogen removal, and then the product gas then combined with the second portion, such that the combined gas stream has ≤0.3% hydrogen in it; and/or
  (ii) oxygen can be added to the methane-containing gas mixture containing residual hydrogen in less than a stoichiometric amount, such that the reaction produces a product gas with ≤0.3% hydrogen in it. This embodiment will be particularly useful if it is desired that the product gas be substantially oxygen free.

A combination of these two alternatives may also be used. Also, the oxidation catalyst may be split into two parts with a portion of the methane-containing gas mixture containing residual hydrogen being fed, together with the oxygen-containing gas, to a first part and a portion of the methane-containing gas mixture containing residual hydrogen fed to the second part, which may be in the same or different oxidation vessel. In this way the level of hydrogen and oxygen in the product gas can be optimised according to requirements. Other combinations can be envisaged by those skilled in the art to manage the relative concentrations of hydrogen and oxygen in the product gas.

The oxidation catalyst is preferably a supported precious metal catalyst. For example the catalyst may comprise one or more of Pt, Pd, Rh, Ir or Ru at 0.1 to 5% by weight on an oxidic support such as alumina, titania, zirconia or silica. Preferably the catalyst comprises Pt or Pd on alumina, e.g. ≤5% wt Pt on alumina. The oxidation catalyst may be in the form of a woven, nonwoven or knitted mesh, tablets, pellets or extrudates, a foam, monolith or coating on an inert support. The precious metal oxidation catalyst is preferably a 0.1 to 5% wt platinum on alumina catalyst, such as Puravoc™ 73, available from Johnson Matthey PLC, but other supported precious metal catalysts may be used.

The oxidation catalyst may be operated at an inlet temperature in the range from 150 to 350° C. and an exit temperature from 150 to 450° C.

The oxidation reaction is exothermic and the reaction may be performed adiabatically in a fixed bed selective oxidation vessel. The flow through the bed may be axial and/or radial flow. The selective oxidation step may alternatively be operated with cooling of the catalyst bed, e.g. by passing a the first feed gas mixture or the hydrogen-containing gas or the carbon dioxide containing gas through one or more tubes disposed within the catalyst bed.

Both the methanation and oxidation catalysts are preferably used in the form of pellets or extrudates with a diameter or width in the range 2-10 mm and an aspect ratio, i.e. length/diameter or width in the range 0.5 to 4. The gas hourly space velocity (GHSV) of the first and/or second feed gas mixtures through the catalyst beds may be in the range 2000 to 20000 $hr^{-1}$.

The process, including the methanation step and the oxidation step, is desirably performed at a pressure in the range 5 to 80 bar abs.

If desired the product methane-containing gas mixture from the oxidation step may be subjected to further processing including drying to remove water and/or carbon dioxide removal. The drying may be performed by cooling the product gas stream to below the clew point and collecting the liquid condensate, optionally with further drying over molecular sieves. The $CO_2$-removal may be accomplished using solvent- or amine-wash, or caustic-wash techniques known in the art. Alternatively pressure-swing adsorption may be used.

The invention is further illustrated by reference to the accompanying drawing in which;

FIG. 1 is a depiction of a flowsheet of one embodiment according to the present invention.

In FIG. 1, a carbon dioxide-containing gas mixture 10 is pre-heated in heat exchanger 12 and passed through a desulphuriser vessel 14 containing fixed bed of a zinc oxide desulphurisation material 16 in to remove hydrogen sulphide and form a desulphurised carbon dioxide-containing gas mixture 18. A hydrogen-containing gas mixture 20 is pre-heated in heat exchanger 22 and the resulting heated gas in line 24 mixed with the desulphurised carbon dioxide-containing gas mixture 18 to form a first feed gas mixture in line 26. The first feed gas mixture 26 is passed at an inlet temperature of 200-350° C. and a pressure of 5-80 bar abs to the inlet of a methanation vessel 28 containing a fixed bed of a particulate nickel-containing methanation catalyst 30. Methanation reactions occur as the gas passes adiabatically through the catalyst bed to form a methane-containing gas mixture containing residual hydrogen 32. The methane-containing gas mixture containing residual hydrogen 32 is passed to a heat exchanger 34 where is it cooled in heat exchange with a coolant to a temperature below about 350° C. The resulting cooled gas mixture 36 is mixed with an oxygen stream fed via line 38 at a temperature of about 30° C. to form a second feed gas mixture 40. The second feed gas mixture 40 is passed at an inlet temperature of 150-350° C. to the inlet of an oxidation vessel 42 containing a fixed bed of a particulate alumina-supported platinum selective oxidation catalyst 44. Oxidation reactions occur as the gas passes adiabatically through the catalyst bed to form a hydrogen-depleted methane-containing gas mixture 46.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

The invention is further illustrated by reference to the following calculated Example.

EXAMPLE 1

1000 kgmols/hr of a hydrogen-containing gas mixture containing 90% by volume methane and 10% by volume hydrogen is mixed with 27.5 kgmols/hr of a desulphurised carbon dioxide gas mixture consisting essentially of carbon dioxide to form a first feed gas mixture. The first feed gas mixture is fed to a methanator containing a bed of Katalco™ CRG-S2R at an inlet temperature of about 250° C. and a pressure of 30 bara. The methanation reaction proceeds to reduce the hydrogen concentration to approximately 1% by volume and heat the reacting gas to about 330° C.

The resultant gas stream is cooled down to 300° C. in a heat exchanger and mixed with 5.9 kgmols/hr of an oxygen-containing gas containing 99.5% oxygen with the resultant gas stream passed to an oxidation vessel containing a bed of Puravoc™ 73 selective oxidation catalyst, where oxygen reacts selectively with hydrogen. The resulting gas has a composition of approx. 93.8% vol $CH_4$, 0.5% vol $CO_2$, 5.6% vol $H_2O$, 800 ppmv oxygen and <100 ppmv hydrogen and leaves the reactor at about 348° C. and 28 bara.

If, alternatively, the resultant gas stream from the methanator is fed to a second methanation stage at about 250° C., then the hydrogen level in the product gas from the oxidation vessel is about 0.36% vol. Hence, the invention allows a significant reduction in the hydrogen level of the product methane containing gas to be achieved in comparison to using a second methanation stage.

The invention claimed is:

1. A process for producing a methane-containing gas mixture comprising the steps of:
   (i) passing a first feed gas mixture comprising hydrogen and carbon dioxide through a bed of methanation catalyst to react a portion of the hydrogen with at least a portion of the carbon dioxide and form a methane-containing gas mixture containing residual hydrogen,
   (ii) adding an oxygen-containing gas to the methane-containing gas mixture containing residual hydrogen to form a second feed gas mixture, and
   (iii) passing the second feed gas mixture through a bed of a selective oxidation catalyst at an inlet temperature in the range 150 to 350° C. to selectively react the residual hydrogen and oxygen to form a hydrogen depleted methane-containing gas mixture.

2. The process according to claim 1, wherein the hydrogen concentration in the first feed gas mixture is 20% by volume.

3. The process according to claim 1, wherein the first feed gas mixture is a synthesis gas comprising hydrogen, carbon dioxide and carbon monoxide.

4. The process according to claim 1, wherein the first feed gas mixture is a prepared by mixing a hydrogen-containing gas mixture with a carbon dioxide-containing gas mixture.

5. The process according to claim 4, wherein the hydrogen-containing gas mixture is a methane-containing gas mixture.

6. The process according to claim 4, wherein the first feed gas mixture or hydrogen-containing gas mixture and/or the carbon dioxide-containing gas mixture are subjected to a desulphurisation step prior to the methanation step.

7. The process according to claim 1, wherein the methanation catalyst is a ruthenium- or nickel-containing methanation catalyst.

8. The process according to claim 1, wherein the methanation catalyst is operated at an inlet temperature in the range 200 to 350° C.

9. The process according to claim 1, wherein the temperature of the methane-containing gas mixture containing residual hydrogen is adjusted before mixing it with the oxygen containing gas.

10. The process according to claim 1, wherein the oxidation catalyst is a supported precious metal oxidation catalyst.

11. The process according to claim 1, wherein the process is performed at a pressure in the range 5 to 80 bar abs.

12. The process according to claim 1, wherein the methanation catalyst is operated at an inlet temperature in the range 200 to 300° C.

13. The process according to claim 1, wherein the methanation catalyst is operated at an inlet temperature in the range 230 to 280° C.

* * * * *